United States Patent [19]

Lippincott, III

[11] Patent Number: 5,938,700
[45] Date of Patent: *Aug. 17, 1999

[54] CONSTRAINED PROSTHESIS FOR REPLACEMENT OF JOINTS BETWEEN LONG BONES IN THE HAND

[75] Inventor: Albert L. Lippincott, III, Prior Lake, Minn.

[73] Assignee: Engineering Consulting Services, Inc., Prior Lake, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 09/022,130

[22] Filed: Feb. 11, 1998

[51] Int. Cl.$^6$ ....................................................... A61F 2/42
[52] U.S. Cl. ................................ 623/21; 623/18; 623/20
[58] Field of Search ................................... 623/21, 20, 19

[56] References Cited

U.S. PATENT DOCUMENTS

| | | |
|---|---|---|
| 3,466,669 | 9/1969 | Flatt . |
| 3,506,982 | 4/1970 | Steffee . |
| 3,638,243 | 2/1972 | Campbell, Jr. et al. . |
| 3,651,521 | 3/1972 | Devas . |
| 3,772,709 | 11/1973 | Swanson . |
| 3,805,302 | 4/1974 | Mathys . |
| 3,869,729 | 3/1975 | Attenborough . |
| 3,946,445 | 3/1976 | Bentley et al. . |
| 3,986,212 | 10/1976 | Sauer . |
| 3,990,118 | 11/1976 | Strickland et al. . |
| 3,991,425 | 11/1976 | Martin et al. . |
| 3,992,726 | 11/1976 | Freeman et al. . |
| 4,011,603 | 3/1977 | Steffee . |
| 4,059,854 | 11/1977 | Laure . |
| 4,106,128 | 8/1978 | Greenwald et al. . |
| 4,194,250 | 3/1980 | Walker . |
| 4,204,284 | 5/1980 | Koeneman . |
| 4,213,208 | 7/1980 | Marne . |
| 4,231,121 | 11/1980 | Lewis . |
| 4,242,759 | 1/1981 | White . |
| 4,276,660 | 7/1981 | Laure . |
| 4,304,011 | 12/1981 | Whelan, III . |
| 4,349,922 | 9/1982 | Agee . |
| 4,352,212 | 10/1982 | Greene et al. . |
| 4,375,703 | 3/1983 | Evans et al. . |
| 4,685,919 | 8/1987 | Niwa et al. . |
| 4,725,280 | 2/1988 | Laure . |
| 4,759,768 | 7/1988 | Hermann et al. . |
| 4,911,719 | 3/1990 | Merle . |
| 4,944,758 | 7/1990 | Bekki et al. . |
| 4,955,916 | 9/1990 | Carignan et al. . |
| 5,007,932 | 4/1991 | Bekki .................................... 623/21 X |
| 5,047,059 | 9/1991 | Saffar . |
| 5,133,761 | 7/1992 | Krouskop . |
| 5,147,386 | 9/1992 | Carignan et al. . |
| 5,290,314 | 3/1994 | Koch et al. . |
| 5,405,399 | 4/1995 | Tornier ...................................... 623/21 |
| 5,405,400 | 4/1995 | Linscheid et al. . |
| 5,405,401 | 4/1995 | Lippincott ................................ 623/21 |

(List continued on next page.)

*Primary Examiner*—David H. Willse
*Assistant Examiner*—Suzette Jackson
*Attorney, Agent, or Firm*—Fredrikson & Byron, PA

[57] ABSTRACT

A joint prosthesis for replacing a joint between two elongated bones of the hand. A first member is provided with an elongated stem for reception in one of the elongated bones and includes a head remote from the stem, the head having a central arcuate dovetail rib arising from a spheroidal convex articulating surface. A second member has a stem for reception in the other bone and a base remote from the stem, the base having a central arcuate dovetail slot formed in a spheroidal concave surface shaped to articulate with the convex articular surface. The central arcuate dovetail rib of the first member and arcuate dovetail slot of the second member are assembled to fully engage and articulate with each other to restrain separation of the members at all degrees of flexion ranging from 0 degrees extension through to 110 degrees of flexion, the force between the members being borne primarily by said spheroidal articular surfaces throughout the range of motion.

5 Claims, 4 Drawing Sheets

U.S. PATENT DOCUMENTS

| | | |
|---|---|---|
| 5,413,609 | 5/1995 | Nicol et al. . |
| 5,425,777 | 6/1995 | Sarkisian et al. . |
| 5,458,647 | 10/1995 | Brochier et al. . |
| 5,522,903 | 6/1996 | Sokolow et al. . |
| 5,549,681 | 8/1996 | Segmuller et al. . |
| 5,549,690 | 8/1996 | Hollister et al. . |
| 5,645,605 | 7/1997 | Klawitter ................................. 623/21 |
| 5,674,297 | 10/1997 | Lane ........................................ 623/21 |
| 5,702,469 | 12/1997 | Whipple et al. . |
| 5,702,471 | 12/1997 | Grundei et al. . |
| 5,702,472 | 12/1997 | Huebner . |

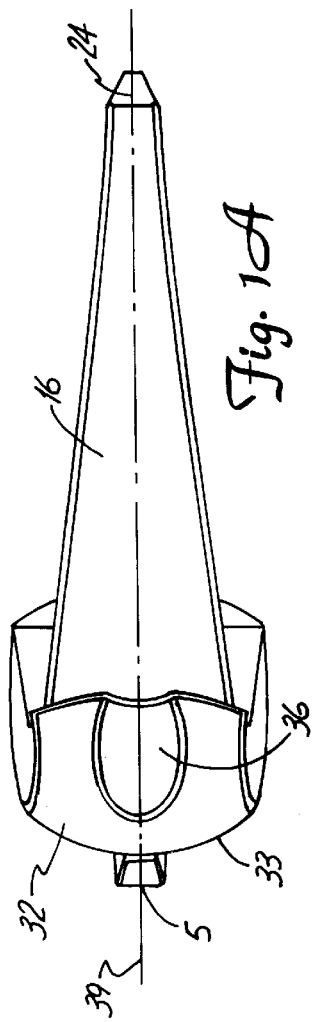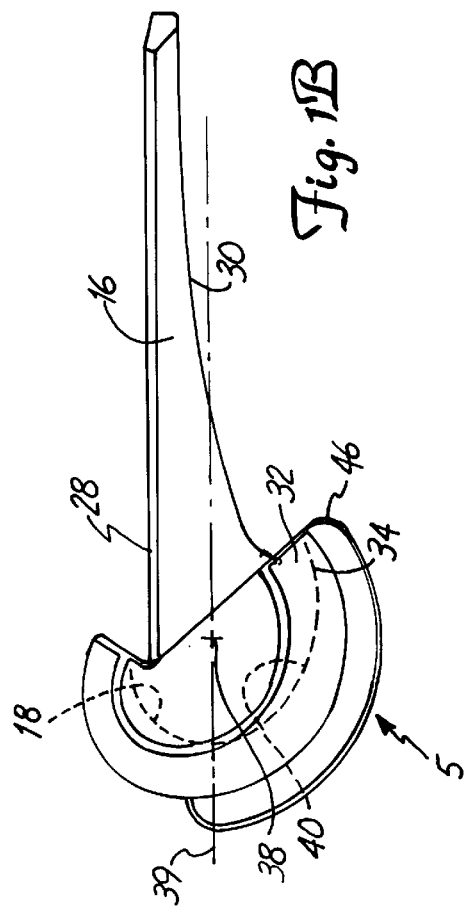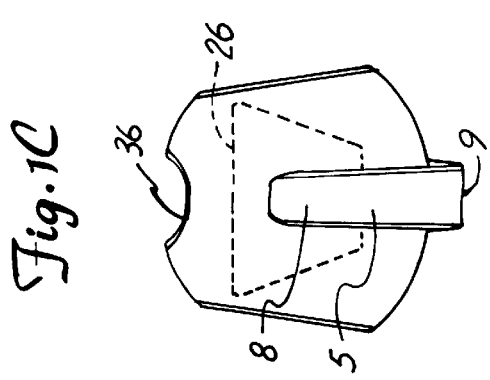

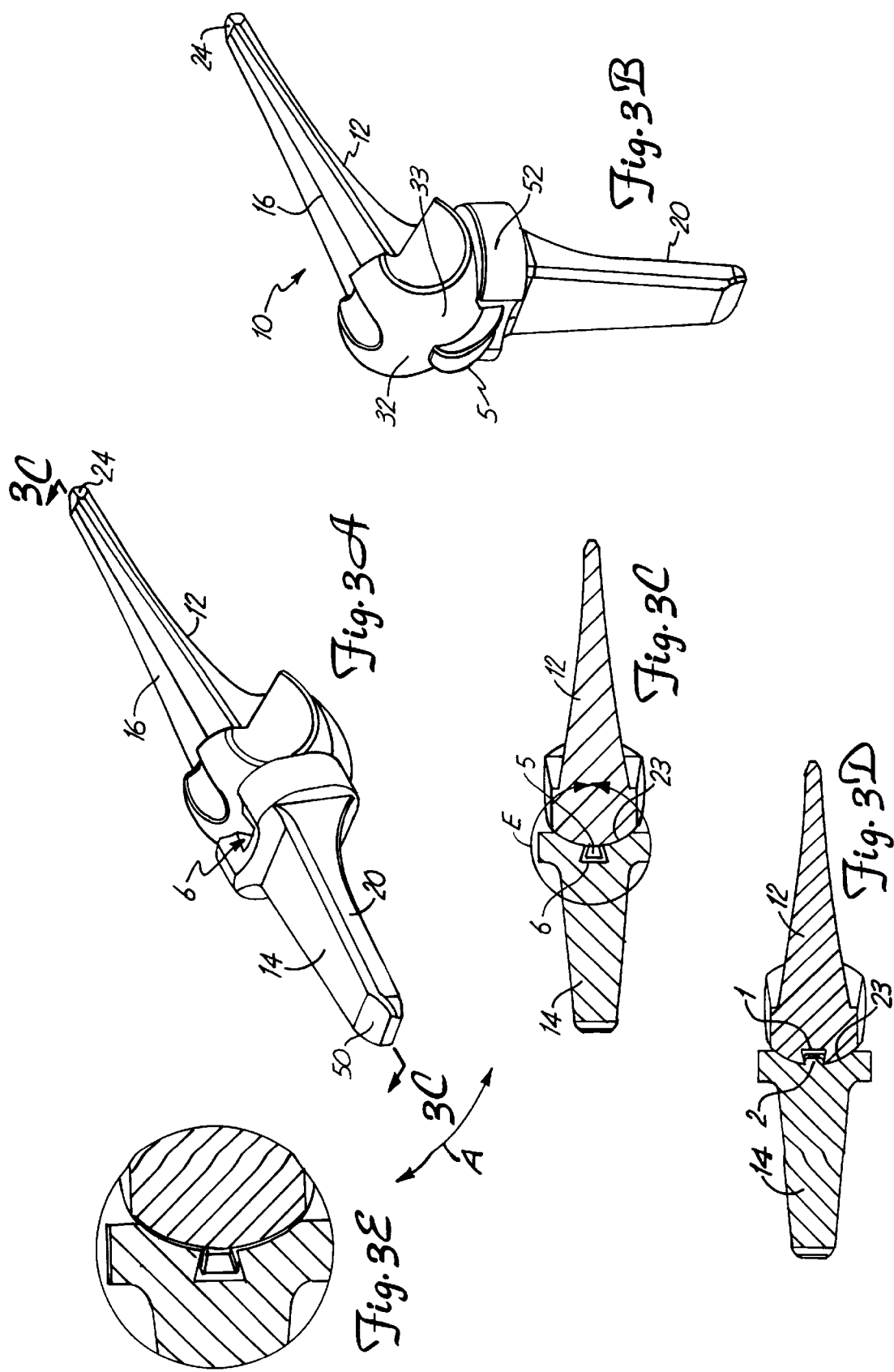

CONSTRAINED PROSTHESIS FOR REPLACEMENT OF JOINTS BETWEEN LONG BONES IN THE HAND

BACKGROUND OF THE INVENTION

This invention relates to joint prosthesis particularly adapted for replacing a joint between two of the long bones of the hand such as the joint between the metacarpal and the first phalanx that articulates with the metacarpal.

The joints between elongated bones of the hand can be damaged by accident or by diseases such as rheumatoid arthritis and osteoarthritis and often need to be surgically replaced. Past procedures for replacing damaged or diseased joints often have involved surgical removal of substantial portions of the bone adjacent a joint's articulating surfaces and implantation of an articulating prosthesis. The surgical procedure often involved removing not only substantial portions of bone but also of soft tissue attachments between the bony ends of the joint. This, in turn, has often required that the articulating ends of the prosthesis be fastened together in such a manner that they are not readily separated. Limited pivoting of the joint in the lateral direction (that is, in the radial/ulnar direction) was permitted in most prostheses of this kind. A finger joint of this general type as shown in Steffee, U.S. Pat. No. 4,001,603 is referred to as a 'constrained hinged' prosthesis.

Other finger joint prosthesis are provided with stems having articulating, opposed heads and in which the heads were permitted lateral pivoting movement with respect to one another. One such prosthesis is shown in White, U.S. Pat. No. 4,242,759. The completely separable articulating heads described in the White patent contained mating ridges and troughs, the contact between the ridges and troughs varying with flexure of the joint. Lippincott U.S. Pat. No. 5,405,401 shows the use of lateral articulating surfaces to restrain the lateral pivoting movement.

It is known that certain arthritis diseases, such as rheumatoid arthritis, can cause severe radial/ulnar cosmetic deformity in the hand. Unfortunately, use of a 'non-constrained' prosthesis design for patients with rheumatoid arthritis would allow postoperative return of severe deformity within joint replacements of the hand. This severe deformity in this type of a non-constrained type of implant could also lead to subluxation or complete dislocation of the two opposed head members resulting in failure of the implant device.

It is desired to provide a prosthesis so configured and arranged that its surgical implantation would not involve substantial disruption of soft tissue connections between the articulating bones nor removal of substantial portions of the bones themselves. Such prostheses would also control the possible return of cosmetic deformity to the hand. Desirably, such prostheses would duplicate closely the articulation afforded by a natural joint.

SUMMARY OF THE INVENTION

It is an object of the invention to provide a joint prosthesis which can readily be implanted without substantial removal of bone nor disruption of soft tissue connections between the bones. Mimicking the normal kinematic movement of normal physiological joints, the prostheses of the invention has as an object the partial restraint of lateral pivoting and full restraint of separation of one bone with respect to the other when the bones are substantially aligned (that is, when the fingers are extended), and the full restraint of such lateral movement and separation when the bones are flexed through a full range of articular motion.

The prosthesis includes a first member having an elongated stem for reception in one of the elongated bones, and a head remote from the stem, the head having a convex generally spheroidal articulating surface. The second member has a stem for reception in the other of the two elongated bones and includes a base remote from the stem, the base of the second member having a generally spheroidal concave articulating surface shaped for articulation with the convex articulating surface of the first member to afford flexion between the members in a given plane from about 0 degrees (when the stems are substantially aligned) through at least about 110 degrees when the joint is fully flexed.

Protruding from the generally spheroidal articulating surface of one of the members, preferably the first prosthesis member, is an elongated, arcuate dovetail rib, and formed in the articulating surface of the other member is an elongated arcuate dovetail slot shaped and configured for continuous reception of the dovetail rib during flexion of the prosthesis to restrain separation of the prosthesis members. The depth of the slot is greater than the height of the rib such that the rib does not bottom out in the slot during flexion of the prosthesis. Desirably, the slot has a width loosely receiving the rib at zero degrees of flexion to enable some lateral articular movement between the members, the rib being larger near one end thereof to restrain lateral articular movement between the members at 110 degrees of flexion. Alternatively, the width of the slot encountered by the rib may gradually decrease toward said one end or the depth of the dovetail slot may decrease toward that end, or both.

The head of the first member and the base of the second member are sufficiently narrow, measured in the radial/ulnar direction, as to avoid any substantial interference with the collateral ligament tissues of the joint, thereby enabling these ligaments to be preserved and to function properly without being traumatized.

DESCRIPTION OF THE DRAWINGS

FIGS. 1A, 1B, and 1C are dorsal, lateral, and distal end views of a first member of a prosthesis of the invention;

FIGS. 3A and 3B are perspective views showing different degrees of articulation of a prosthesis of the invention employing the first and second member.

FIG. 3C is a cross-sectional view taken along line C—C of FIG. 3A;

FIG. 3D is a cross-sectional view similar to that of FIG. 3C but showing a modified embodiment;

FIG. 3E is an enlarged, broken-away cross section of circle E of FIG. 3C; and

DESCRIPTION OF THE PREFERRED EMBODIMENT

For ease of understanding, the invention is described below with reference to the metacarpal/phalanx joint.

Figure 4:
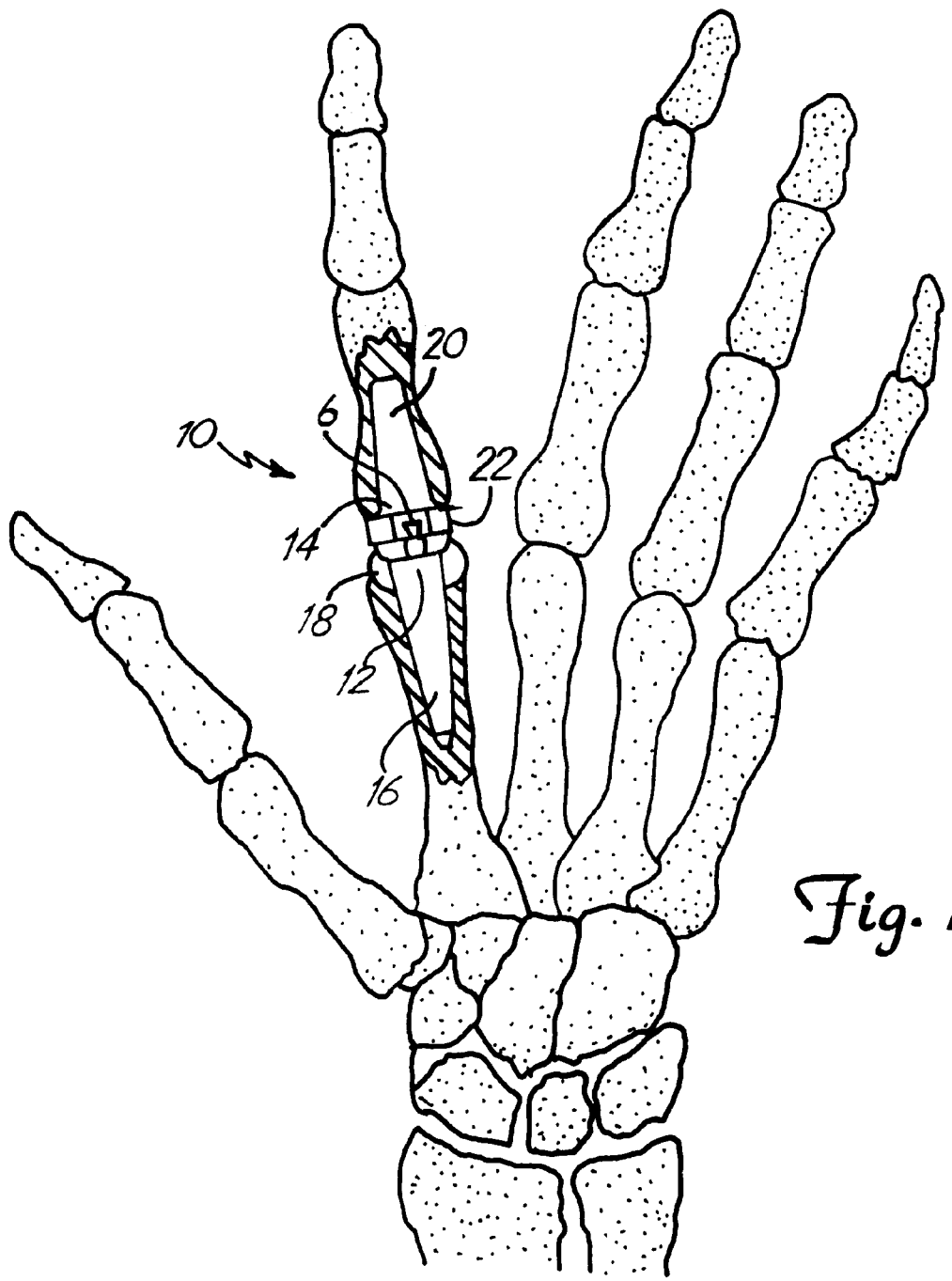
FIG. 4 is a broken-away dorsal view of the bones of the hand showing a prosthesis of the invention as implanted.

Referring first to FIGS. 3A, 3B and 4, a prosthesis of the invention is shown at 10 as comprising a first member 12 and a second member 14. Member 12 includes a stem 16 for reception in the marrow cavity at the distal end of a metacarpal, a head 32 having a spheroidal articulating surface 33 and a center arcuate dovetail rib 5. Member 14 includes a stem 20 for reception in the marrow cavity at the proximal end of a phalanx, and includes a head 52 having a convex, generally spheroidal surface 23 and a center arcuate dovetail slot 6, the articulating concave surface shown generally as 23 being curved to articulate with the surface 33 of the first member. The protruding dovetail rib 5 of the first member engages in the recessed dovetail slot 6 of the second member so that the two members cannot be separated when in use.

Member 12 shown in FIGS. 3A and 3B is depicted in greater detail in FIGS. 1A, 1B, and 1C. Stem 16 has a sharpened proximal end 24 for insertion and guidance in the medullary cavity. Desirably, it is generally trapazoidal in cross section as shown at 26 in FIG. 1C. The stem has dorsal and volar surfaces 28, 30 (FIG. 1B), and extends generally in a plane parallel to the dorsal surface of the bone (not shown) of the metacarpal into which is to be inserted.

At its distal end, the stem 16 is provided with an enlarged head 32 having a centered arcuate dovetail rib 5 arising from a convex, spheroidal, distally facing surface 33. Surface 33 extends toward the palmar direction and then more sharply proximally as shown at 34 in FIG. 1B. The dorsal facing portion of the surface 33 is provided with an elongated groove 36 to aid in proper orientation of the member 12 during implantation and also to receive the extensor mechanism soft tissues.

Spherical surface 33 is formed about a point 38 as shown in FIG. 1B and it will be noted from FIG. 1B that the stem 16 is spaced dorsally from axis 39 so as to more closely approach the normal anatomy of the distal end of the metacarpal. If desired, the head 32 has an interior surface 18 formed as a generally hemispherical shell having a recessed, inner surface 40 (FIG. 1B) to which the proximal end of the stem 16 is attached, as by welding or, more preferably, by investment casting as a solid piece. The distal end of the metacarpal may be surgically sculpted so as to be received within the recessed head 18, thereby reducing the amount of bone that must be removed. If desired, the head may be made solid, that is, not recessed, for the purpose of reducing the difficulty in the manufacture of this head shape and allow simple surgical bone removal in surgery.

Extending proximally and centrally from the distal spheroidal surface 33 is a protruding dovetail rib 5. This configuration, as shown best in FIG. 1B, is distally facing and starts near the axis 39 and then curves volarly and proximally (in the direction of the stem) as shown at 46 in FIG. 1B. The dovetail then ends at the extreme volar side of the spheroidal surface 33. As shown in FIG. 1C, the protruding dovetail 5 is narrowest at the extreme dorsal aspect 8 and tapers slightly to a broader width 9 as the dovetail revolves around head surface 33 to the extreme volar side 46 where the dovetail 5 is the greatest width.

Figure 2C:
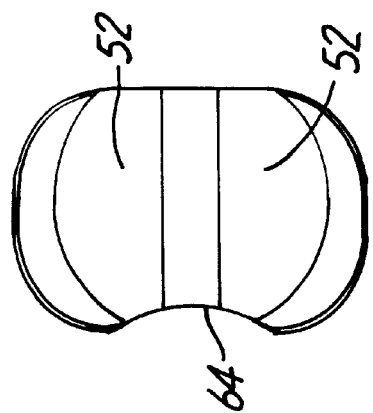
FIGS. 2A, 2B, and 2C are dorsal, lateral and proximal end views of a second member of the prosthesis of the invention.
Figure 2A:
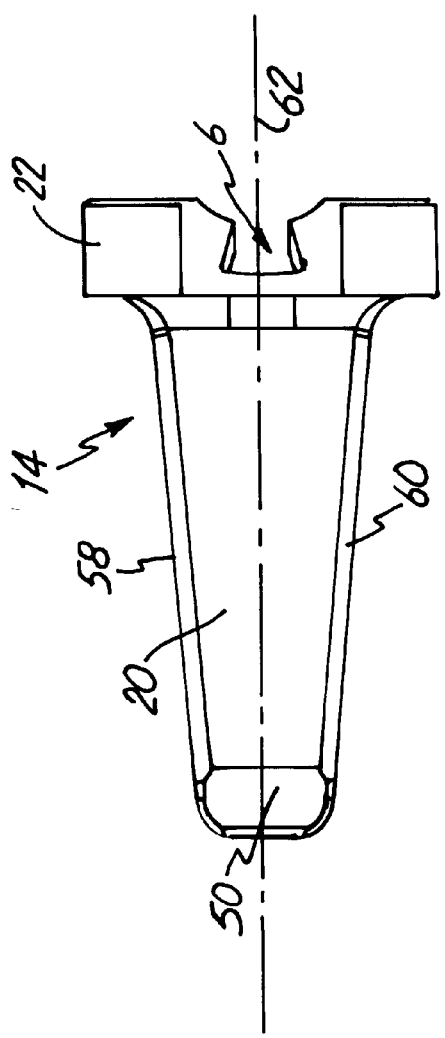
Figure 2B:
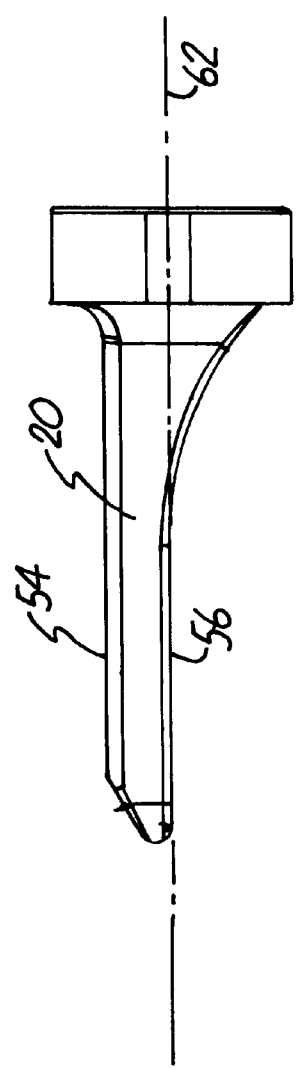

FIGS. 2A, 2B, and 2C depict the second member 14 of the prosthesis, this member having a base 22 and a stem 20. Stem 20 is rectangular in cross section, tapering distally to a sharpened end 50 receivable and guided into the marrow canal at the proximal end of a proximal or first phalanx. The stem terminates distally (with respect to the anatomy of the hand) in the base 22; the latter having a centered recessed arcuate dovetail slot 6 formed in a concave, desirably generally spheroidal and proximally facing articulating surface 52. The rectangular stem 50 has generally broad, flat dorsal and volar sides 54, 56 and narrower, distally converging lateral sides 58, 60. Viewed from the dorsal side as in FIG. 2A, the stem and typically the base 22 are symmetrical with respect to the axis 62 of the spheroidal, proximally facing articulating surfaces 52. As shown in FIG. 2B, however, the stem 20 is offset dorsally from the axis 62 so as to better conform to the anatomy of the proximal end of the (first) phalanx.

The base 22 of the second member 14 includes a centrally located longitudinally extending groove 64 in the dorsal aspect as shown in FIG. 2C to aid in proper orientation of the member 14 during implantation and also to receive the extensor mechanism soft tissues.

Referring back now to FIG. 3A, the concave recess arcuate dovetail slot 6 formed in the spheroidal surface 52 of the base 22 of second member 14 is shaped to receive in mating fit and articulating contact the convex protruding arcuate dovetail rib 5 arising from the two adjacent spheroidal distally facing surface 33 of the head 32 when the members 12 and 14 are assembled and implanted in the confronting ends of the metacarpal and proximal (first) phalanx bones of the hand. The proximal dorsal ends of the arcuate dovetails 6 and 5 are assembled and show a difference in dovetail size, so that the concave recess dovetail slot 6 is larger in width than that of convex protruding dovetail rib 5 when the stems 16, 20 of these members are generally aligned (as when the fingers are extended) allowing some lateral pivoting movement of the phalanx as shown by arrow A in FIG. 3A. Such lateral pivoting movement may cause the articulating spheroidal surfaces at one side of the dovetail mechanism to separate slightly. Contact between the mating angled sides of dovetails 5 and 6 respectively, limit the amount of radial/ulnar lateral movement afforded the stem 20 when the fingers are extended. This looseness in fit between the dovetails is shown in FIG. 3C.

As the assembled phalanx base 22 is revolved around the mating spheroidal head 32, the convex arcuate dovetail rib 5 is tapered in dimension to match in size the convex recess of the arcuate dovetail slot 6 when the stems 16, 20 of these members are rotated through 110 degrees as when the fingers are flexed 110 degrees as shown in FIG. 3B. When flexion of the finger has reached 110 degrees, the primary load between the two members is still borne by the adjacent articulating surfaces 33 and 52 of members 12 and 14, respectively. With the contact and matching sizes of the dovetails 5 and 6 at the 110 degree flexion, radial/ulnar lateral pivoting of the second member 14 with respect to the first member 12 is substantially and desirably completely restrained.

Reversal of the constraining feature in the dovetails can be chosen as shown in FIG. 3D. In this section view, a recessed arcuate dovetail slot 1 is formed in the first member 12 while a protruding arcuate dovetail rib 2 is in the second member 14. FIG. 3E also shows the looseness in fit between the dovetails while in extension so as to allow a lateral restrained movement of up to 20 degrees from the center line. The recessed arcuate dovetail slot 5 is tapered in width so as to allow pivotal lateral movement while in extension and taper to a greater width when in full 110 degree flexion so as to allow no lateral movement, as previously explained.

Throughout the mating fit and movement of the dovetail mechanism, in either mating configuration, the geometry of the dovetail configuration will allow no seizing in arcuate movement of the two members 12 and 14. In other words, there will be a minimal amount of looseness between the mating dovetails when fully flexed at 110 degrees.

The first and second members of the prosthesis of the invention may be manufactured from any of the materials that have been found acceptable for use in articulating prostheses, including, for example, ultra high molecular weight polyethylene, stainless steel, and various metal alloys. The first member, for example, can be made from metal material and the second from a composite ultra high molecular weight polyethylene/metal combination. For strength and wear factors, it may be desired that the articulating surfaces of the mating members both be made of a wear-resistant metal or ceramic combination from wear-resistant materials. Surface treatments, e.g., titanium nitride, ion bombardment, and diamond like carbon coatings, may assist in superior wear resistance of the articulating surfaces.

For implantation, a straightforward procedure is employed. Surgical access to the metacarpal/phalanx joint is performed dorsally. The bony segments are exposed, care being taken to preserve as much as possible bone with its soft tissue connections. The opposing bone ends are surgically sculpted to receive the head 32 and base 22 of the first and second members, respectively, care again being taken to avoid damage to soft tissue connections. Surgical access also is gained to the marrow cavities of the respective bones, the cavities being sculpted using specialized surgical instrumentation such as burrs, broaches and trial prostheses to receive the stem of the prosthesis members. The stems of each member are aligned, and implanted in the marrow cavities using bone cement in the usual fashion. Once the cement has hardened, the mating dovetails are aligned, the distal digit hyper-extended in relation to the proximal to enable dovetail assembly before closure.

It is contemplated that it may be appropriate in some circumstances to cause the stems of the prosthesis members to fit fairly tightly in the marrow cavities of the bone in which they are implanted, omitting the need for bone cement. In this event, the surfaces of the stems desirably are shaped or treated to encourage bone ongrowth or ingrowth, as by providing the stems with porous surfaces or by applying to the stems a cell adhesion promoter such as collagen or the like.

Use of this constrained finger implant is not confined to the MCP knuckle joint but may find design function/application in other joint areas of the hand such as the PIP and DIP joints of the fingers and PIP and DIP joints of the thumb.

While a preferred embodiment of the present invention has been described, it should be understood that various changes, adaptations and modifications may be made therein without departing from the spirit of the invention and the scope of the appended claims.

What is claimed is:

1. A joint prosthesis for replacing a joint between two articulating elongated bones of the hand, comprising a first prosthesis member having an elongated stem for reception in one of the elongated bones and a head remote from the stem, the head having a convex generally spheroidal articulating surface, a second prosthesis member having a stem for reception in the other of the two elongated bones and a base remote from the stem, the base having a concave, generally spheroidal articulating surface shaped for articulation with the convex articulating surface of the first member to afford flexion of the joint prosthesis, an elongated, arcuate dovetail rib protruding from the articulating surface of one of the members, and an elongated arcuate dovetail slot formed in the articulating surface of the other member, the slot being shaped and configured for continuous reception of the dovetail rib during flexion of the prosthesis to restrain separation of the prosthesis members throughout the range of flexion, said slot being configured to loosely receive the rib at zero degrees of flexion to enable limited lateral articular movement between the members, the slot near one end thereof being configured to more closely receive the rib to restrain lateral articular movement between the members at 110 degrees of flexion.

2. The joint prosthesis of claim 1 wherein the depth of the slot is greater than the height of the rib such that the rib does not bottom out in the slot during flexion of the prosthesis.

3. The joint prosthesis of claim 1 wherein said slot is configured to enable lateral movement through an angle of at least 20 degrees at zero degrees of flexion.

4. The joint prosthesis of claim 1 wherein said rib protrudes from the convex articular surface of the first prosthesis member.

5. The joint prosthesis of claim 1 wherein said rib protrudes from the concave surface of the second prosthesis member.

* * * * *